US00PP36948P2

(12) United States Plant Patent
Koot

(10) Patent No.: US PP36,948 P2
(45) Date of Patent: Sep. 9, 2025

(54) ***PETUNIA* PLANT NAMED 'Dopetpoplublasa'**

(50) Latin Name: ***Petunia* X *hybrida***
Varietal Denomination: Dopetpoplublasa

(71) Applicant: DUMMEN GROUP B.V., De Lier (NL)

(72) Inventor: Arjan Koot, Oeffelt (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/054,264

(22) Filed: Feb. 14, 2025

(51) Int. Cl.
*A01H 5/02* (2018.01)
*A01H 6/82* (2018.01)

(52) U.S. Cl.
USPC ..... Plt./356.1
CPC ..... *A01H 6/824* (2018.05); *A01H 5/02* (2013.01)

(58) Field of Classification Search
USPC ..... Plt./356.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Petunia* plant named 'Dopetpoplublasa', characterized by its semi-upright and uniformly mounding plant habit; relatively moderately vigorous growth habit and moderate growth rate; freely branching habit; early and freely flowering habit; large velvety dark greyish purple-colored flowers that appear to be almost black in color; good container and garden performance; and resistance to Tobacco Mosaic Virus.

1 Drawing Sheet

Botanical designation: *Petunia* X *hybrida.*
Cultivar denomination: 'DOPETPOPLUBLASA'.

BACKGROUND OF THE INVENTION

The present invention relates to a new and distinct cultivar of *Petunia* plant, botanically known as *Petunia* X *hybrida* and hereinafter referred to by the name 'Dopetpoplublasa'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July 2021 in Rheinberg, Germany of a proprietary selection of *Petunia* X *hybrida* identified as code number TT21-K0351, not patented, as the female, or seed, parent with a proprietary selection of *Petunia* X *hybrida* identified as code number TT21-K0621, not patented, as the male, or pollen, parent. The new *Petunia* plant was discovered and selected by the Inventor as a single flowering plant from within the progeny of the stated cross-pollination in a controlled greenhouse environment in Rheinberg, Germany in April 2022.

Asexual reproduction of the new *Petunia* plant by terminal vegetative cuttings in a controlled greenhouse environment in Rheinberg, Germany since April 2022 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetpoplublasa'. These characteristics in combination distinguish 'Dopetpoplublasa' as a new and distinct *Petunia* plant:

1. Semi-upright and uniformly mounding plant habit.
2. Relatively moderately vigorous growth habit and moderate growth rate.
3. Freely branching habit.
4. Early and freely flowering habit.
5. Large velvety dark greyish purple-colored flowers that appear to be almost black in color.
6. Good container and garden performance.
7. Resistant to Tobacco Mosaic Virus.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more vigorous and stronger than plants of the female parent selection.
2. Plants of the new *Petunia* are more freely branching than plants of the female parent selection.
3. Plants of the new *Petunia* have dark greyish purple-colored flowers that appear to be almost black in color whereas plants of the female parent selection have dark greyish purple (appearing to be almost black) and yellow bi-colored flowers.

Plants of the new *Petunia* can be compared to plants of the male parent selection. In side-by-side comparisons, plants of the new *Petunia* differ primarily from plants of the male parent selection in flower color as plants of the new *Petunia* have dark greyish purple-colored flowers that appear to be almost black in color whereas plants of the male parent selection have purple and yellow bi-colored flowers.

Plants of the new *Petunia* can be compared to plants of *Petunia sensu wijsman* 'DRAY68', disclosed in U.S. Plant Pat. No. 25,931. In side-by-side comparisons, plants of the new *Petunia* and 'DRAY68' differ primarily in the following characteristics:

1. Plants of the new *Petunia* are not as vigorous as plants of 'DRAY68'.
2. Plants of the new *Petunia* have shorter internodes than plants of 'DRAY68' giving a denser appearance.
3. Flowers of plants of the new *Petunia* are more rounded than and not as star-shaped as flowers of plants of 'DRAY68'.
4. Plants of the new *Petunia* are resistant to Tobacco Mosaic Virus whereas plants of 'DRAY68' are not resistant to Tobacco Mosaic Virus.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Dopetpoplublasa' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks from planting rooted young plants when the photograph was taken and 25 weeks from planting rooted young plants when the description was taken. In the following description, color references are made to The Royal Horticultural Society Colour Chart, Fifth Edition, except where general terms of ordinary dictionary significance are used.

Botanical classification: *Petunia* X *hybrida* 'Dopetpoplublasa'.

Parentage:

*Female, or seed, parent*.—Proprietary selection of *Petunia* X *hybrida* identified as code number TT21-K0351, not patented.

*Male, or pollen, parent*.—Proprietary selection of *Petunia* X *hybrida* identified as code number TT21-K0621, not patented.

Propagation:

*Type*.—By terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Semi-upright and uniformly mounding plant habit; freely branching habit with about six primary lateral branches each with about six to seven secondary branches developing after pinching; relatively moderately vigorous growth habit and moderate growth rate.

*Plant height, soil level to top of foliar plane*.—About 27.5 cm.

*Plant height, soil level to top of floral plane*.—About 28 cm.

*Plant diameter*.—About 46 cm.

Lateral branch description:

*Length*.—About 28.5 cm.

*Diameter*.—About 4 mm.

*Internode length*.—About 1.6 cm.

*Strength*.—Moderately strong.

*Aspect*.—Initially upright to somewhat outwardly spreading to eventually trailing.

*Texture and luster*.—Pubescent; semi-glossy.

*Color, developing*.—Close to 144A.

*Color, developed*.—Close to 144B.

Leaf description:

*Arrangement*.—Before flowering, alternate; after flowering, opposite; simple.

*Length*.—About 5.3 cm.

*Width*.—About 2.1 cm.

*Shape*.—Spatulate.

*Apex*.—Obtuse.

*Base*.—Attenuate.

*Margin*.—Entire.

*Texture and luster, upper and lower surfaces*.—Pubescent; leathery; semi-glossy.

*Venation pattern*.—Pinnate; arcuate.

*Color*.—Developing leaves, upper surface: Close to 137A. Developing leaves, lower surface: Close to 137C. Fully expanded leaves, upper surface: Close to 137A; venation, close to 143B. Fully expanded leaves, lower surface: Close to 138A; venation, close to 137C.

*Petioles*.—Length: About 1.4 cm. Diameter: About 2.6 mm. Strength: Moderately strong; firm. Texture and luster, upper and lower surfaces: Smooth, glabrous; matte. Color, upper surface: Close to 143B. Color, lower surface: Close to 143C.

Flower description:

*Flower type and flowering habit*.—Single salverform flowers arising from leaf axils; freely flowering habit with usually about 248 flowers and flower buds developing per plant during the flowering season; flowers face mostly upright to somewhat outwardly.

*Fragrance*.—None detected.

*Natural flowering season*.—Plants flower continuously during the spring and summer in Germany; early flowering habit, plants typically beginning flowering about eleven weeks after planting.

*Flower longevity*.—Depending on temperature and light levels, individual flowers last about two to six days on the plant; flowers persistent.

*Flower buds*.—Length: About 4.3 cm. Diameter: About 7 mm. Shape: Ovoid. Texture and luster: Rippled; semi-glossy. Color: Close to 187A and 200A.

*Flower diameter*.—About 5.3 cm by 6.1 cm.

*Flower depth* (*height*).—About 5.6 cm.

*Flower throat diameter*.—About 1.1 cm.

*Flower tube length*.—About 2.8 cm.

*Flower tube diameter, proximally*.—About 6 mm.

*Corolla*.—Arrangement: Five petals fused at the base and opening into a flared trumpet. Petal lobe length (from throat): About 3.2 cm. Petal lobe width: About 2.6 cm. Petal shape: Roughly spatulate. Petal apex: Obtuse. Petal margin: Entire; slightly undulate. Petal texture and luster, upper and lower surfaces: Rippled, glabrous; velvety; semi-glossy. Throat texture and luster: Rippled, glabrous; semi-glossy. Tube texture and luster: Rippled, glabrous; semi-glossy. Color: Petal lobe, when opening and fully opened, upper surface: Close to 202A; venation, close to 202A; color becoming closer to 187A with subsequent development. Petal lobe, when opening and fully opened, lower surface: Close to 187A; venation, close to 187A; color does not change with subsequent development. Flower throat: Close to 202A; venation, close to 202A. Flower tube: Close to 200A; venation, close to 187A.

*Sepals*.—Arrangement: Five sepals fused at the base forming a tubular star-shaped calyx. Length: About 2.2 cm. Diameter: About 3 mm. Shape: Oblong. Apex: Rounded. Base: Decurrent. Margin: Entire. Texture and luster, upper and lower surfaces: Smooth, glabrous; semi-glossy. Color: When opening, upper surface: Close to 138A. When opening, lower surface: Close to 144A. Fully opened, upper surface: Close to 137A. Fully opened, lower surface: Close to 137C.

*Peduncles*.—Length: About 2.9 cm. Diameter: About 1.6 mm. Strength: Moderately strong. Texture and luster: Smooth, glabrous; semi-glossy. Color: Close to 144A.

*Reproductive organs*.—Stamens: Quantity per flower: Five. Filament length: About 1.9 cm. Filament color: Close to 187B. Anther length: About 1 mm. Anther shape: Ovate. Anther color: Close to 188C. Pollen amount: Abundant. Pollen color: Close to 188B. Pistils: Quantity per flower: One. Pistil length: About 2.1 cm. Style length: About 1.7 cm. Style color: Close to 145B. Stigma diameter: About 2 mm. Stigma shape: Rounded. Stigma color: Close to 143C. Ovary color: Close to 187A. Fruits: Quantity produced per plant: About 24 during the flowering season. Length: About 5 mm. Diameter: About 3.5 mm. Texture: Smooth, glabrous. Color: Close to 161A. Seeds: Quantity per flower: About 25. Length: About 0.5 mm. Diameter: About 0.5 mm. Texture: Smooth, glabrous. Color: Close to 200A.

Garden performance: Plants of the new *Petunia* have been observed to have good garden performance and tolerate wind, rain, temperatures ranging from about 3° C. to about 28° C. and to be suitable for USDA Hardiness Zone 11.

Pathogen resistance: Plants of the new *Petunia* have been observed to be resistant to Tobacco Mosaic Virus. To date, plants of the new *Petunia* have not been observed to be resistant to other pathogens common to *Petunia* plants.

It is claimed:

1. A new and distinct *Petunia* plant named 'Dopetpoplublasa' as herein illustrated and described.

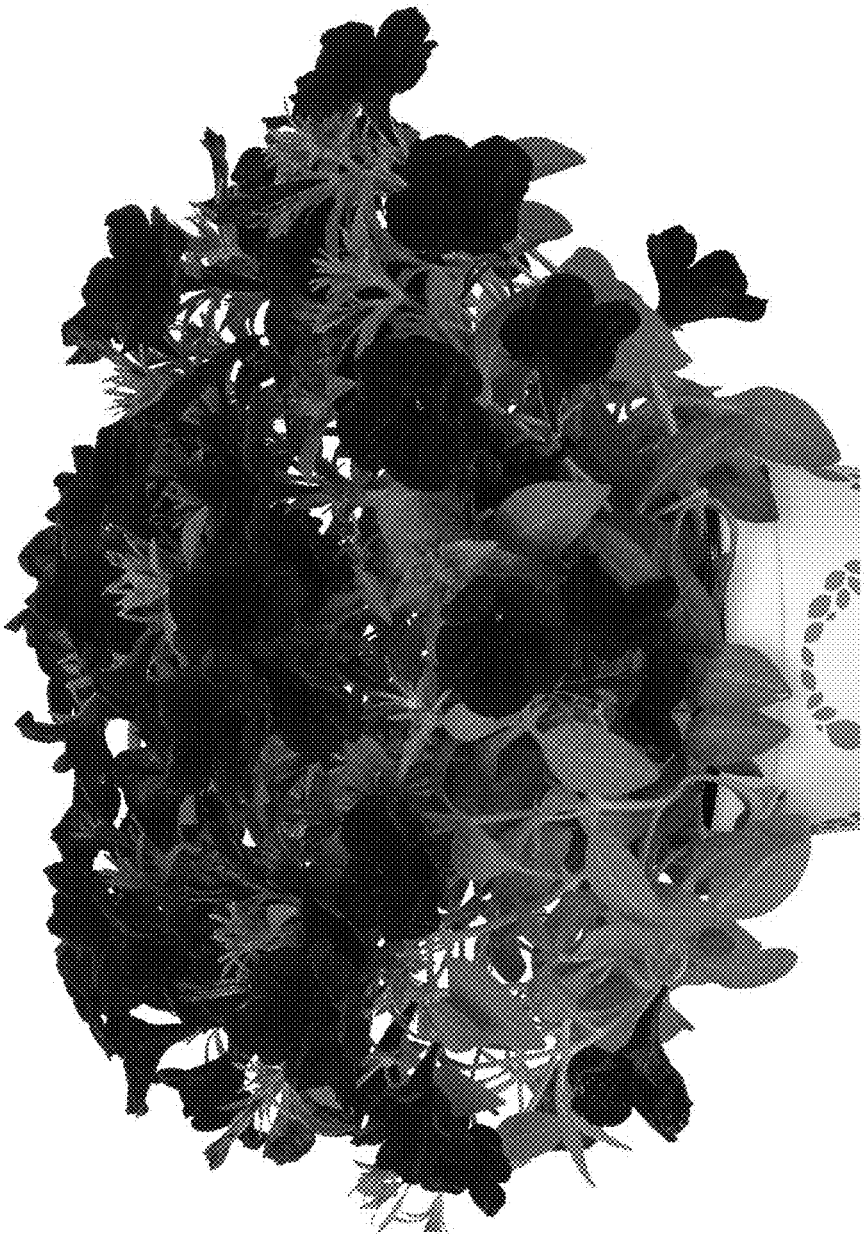

* * * * *